United States Patent [19]

Nobuhara et al.

[11] Patent Number: 4,548,900

[45] Date of Patent: Oct. 22, 1985

[54] METHOD OF INTERFERON PRODUCTION

[75] Inventors: Masahiro Nobuhara, Iwatsuki; Kiyoshi Yamaguchi, Kawaguchi; Ei Mochida, Tokyo, all of Japan

[73] Assignee: Mochida Pharmaceutical Co., Ltd., Tokyo, Japan

[21] Appl. No.: 496,506

[22] Filed: May 20, 1983

[30] Foreign Application Priority Data

May 31, 1982 [JP] Japan ................................. 57-92583

[51] Int. Cl.$^4$ ......................... C12P 21/00; C12N 5/00; C12N 5/02; C12R 1/91
[52] U.S. Cl. ..................................... 435/68; 435/240; 435/241; 435/948; 424/85
[58] Field of Search ................ 435/68, 240, 241, 948, 435/188; 424/85

[56] References Cited

U.S. PATENT DOCUMENTS

| | | | |
|---|---|---|---|
| 3,413,198 | 11/1968 | Deutsch | 435/188 |
| 3,876,375 | 4/1975 | Maurukas et al. | 435/188 |
| 4,266,024 | 5/1981 | Swetly et al. | 424/85 |
| 4,462,940 | 7/1984 | Hanisch et al. | 424/85 |

FOREIGN PATENT DOCUMENTS

| | | | |
|---|---|---|---|
| 0014050 | 8/1980 | European Pat. Off. | 424/85 |
| 0017570 | 10/1980 | European Pat. Off. | 424/85 |
| 3319714 | 12/1983 | Fed. Rep. of Germany | 435/68 |

OTHER PUBLICATIONS

A. D. Inglot et al., Use of PEG-Treated Calf Serum for Cell Cultures in Virus and Interferon Studies, Acta. Virology 19: 250–254, 1975.

*Primary Examiner*—Thomas G. Wiseman
*Assistant Examiner*—Jayme A. Huleatt
*Attorney, Agent, or Firm*—Parkhurst & Oliff

[57] ABSTRACT

A method for the mass production of interferon, wherein cultured cells are brought into contact with at least one polyhydric alcohol, thereby achieving a remarkable increase in the production of interferon from the cultured cells.

25 Claims, 3 Drawing Figures

METHOD OF INTERFERON PRODUCTION

BACKGROUND OF THE INVENTION

This invention relates to a method for mass production of interferon which comprises contacting cultured cells with polyhydric alcohol.

Interferon was discovered by Nagano et al. (Compt. Rend. Soc. Biol., Vol. 148, p. 1700, 1954) and Isaacs et al., (Proc. Roy. Soc. Ser. B, Vol. 147, p. 258, 1957). Recently, it has been reported that interferon has various biological activities such as anti-tumor effects (Gressor et al., B. B. A., Vol. 516, p. 231, 1978), in addition to anti-viral activity, and attention has been given to its possible use as a therapeutic agent. Interferon is classified roughly into 3 groups. These groups are named interferon-α, interferon-β, and interferon-γ (Nature, Vol. 286, p. 110, 1980).

Interferon-α is induced by stimulating cultured leukocytes or lymphoblastoid cells with various viruses such as Sendai virus (HVJ), Newcastle disease virus (NDV), and influenza virus.

Interferon-β is induced by stimulating normal diploid cells with various viruses such as HVJ, NDV, and influenza virus, or with double-stranded RNA, etc. This method has been improved markedly in recent days. For example, the superinduction method by Vilcék, et al. (Antimicrob. Ag. Chemother., Vol. 2, p. 476, 1972), which comprises stimulating the cells with inducers such as double-stranded RNA and thereafter treating them with metabolic inhibitors such as cycloheximide and actinomycin D, remarkably enhances the production of interferon-β.

Interferon-γ is induced by stimulating T lymphocytes with mitogens such as phytohemagglutinin (PHA) and concanavalin A (Con A) or with antigen-antibody reactions.

It is also known that the production of interferon is enhanced by overnight incubation of cells in a medium containing interferon prior to stimulation with the various inducers. This is the so-called priming effect.

SUMMARY OF THE INVENTION

The object of this invention is to provide a method for mass production of interferon from cultivation of cells. Namely, this invention provides an improved method for producing high units of interferon comprising contacting cultured cells with at least one polyhydric alcohol.

More specifically, the object of this invention is to provide a method for producing interferon wherein cultured cells are brought into contact with the polyhydric alcohol by adding the alcohol to a priming medium, induction medium and/or production medium.

A further object of this invention is to provide a method for producing interferon, wherein cultured cells are brought into contact with said alcohol by transient exposure of the cells to a solution of said alcohol at an appropriate stage.

A still further object of this invention is to provide a method for producing interferon, wherein the cultured cells are contacted with the polyhydric alcohol by both the addition of said alcohol to the culture medium and the exposure of the cultured cells transiently to a solution containing said alcohol at an appropriate stage.

DETAILED DESCRIPTION OF THE INVENTION

Figure 1:
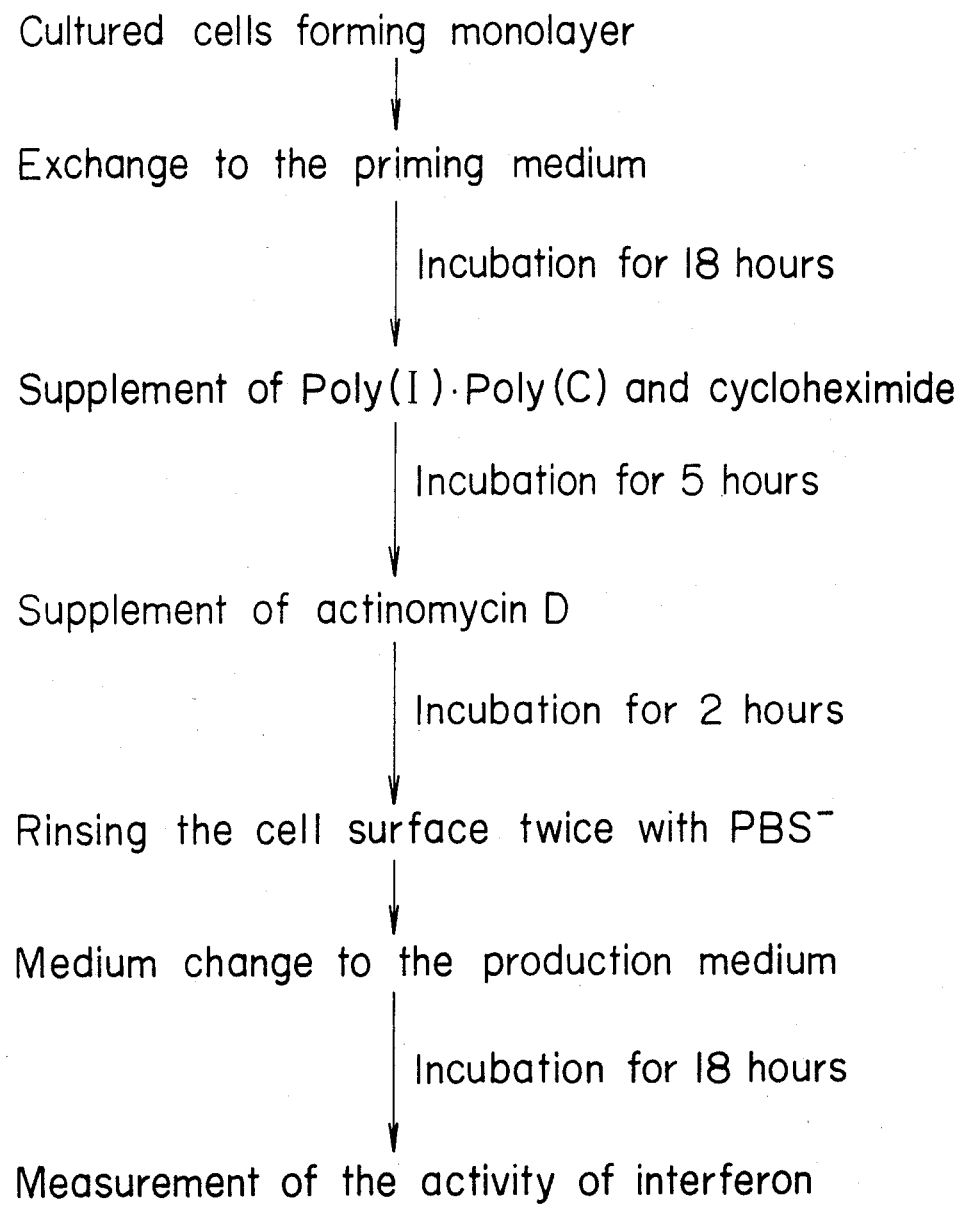
FIG. 1 is a flow chart showing a general process of producing interferon-β which is employed in Experiment 1.

According to this invention, cultured cells are brought into contact with a solution containing at least one polyhydric alcohol. This contact may be performed by adding the alcohol to a priming medium, induction medium and/or production medium. Alternatively, the cultured cells may be transiently exposed to the solution of polyhydric alcohol at an appropriate stage such as by rinsing at the time of medium change. The rinsing may be performed before the medium is changed to a priming medium, induction medium, and/or production medium. The addition of the alcohol to the medium and the rinsing of the cells with the alcohol can be performed in combination.

Polyhydric alcohols useful in this invention are those which have two or more alcoholic hydroxyl groups (—OH) in a molecule. Alcohols of high molecular weight may be used provided that they are soluble in the medium, etc., and show no cytotoxicity at their useful concentrations. For example, the following alcohols may be used: polyethylene glycol (average molecular weight: 200~20,000), diol-type polypropylene glycol (average molecular weight: 1,000~3,000), triol-type polypropylene glycol (degree of polymerization: 500~2,000), ethylene glycol, propanediol, glycerine, butanediol, butanetriol, butanetetrol, pentanediol, pentaerythritol and hexanetriol. Among these alcohols, polyethylene glycol is most preferred.

Since the effective concentration of the polyhydric alcohol depends on the kinds of cultured cells, culture medium, inducers, and polyhydric alcohols to be employed, the most appropriate concentration for each case can be easily determined experimentally. In general, however, about 0.001~30 weight %, preferably about 0.1~5 weight % is applicable for addition to the medium, and about 0.1~60 weight %, preferably about 1~30 weight % is applicable for transient exposure of cultured cells.

The use of a single polyhydric alcohol usually gives sufficient effect. However, a mixture of two or more such alcohols may be used if desired.

Calls which may be used for the production of interferon according to the invention include human diploid MRC-5 cells, human lymphoblastoid Namalva cells, mouse L929 cells and human T cells. In addition, other human cells such as WI-38 cells, IMR-90 cells, MG-63 cells, Flow 1000 cells, Flow 4000 cells and Ball-1 cells are useful for the production of interferon. Other mammalian cells such as RK-13 cells and MDBK cells may be used as well as various mammalian primary culture cells. These exemplary cells are well known in the art and can be obtained by a conventional culture technique or are available when they are of an established cell line from, for example, Dainippon Pharmaceutical Co., Ltd., Osaka, Japan; ATCC; or Hayashibara Biology and Chemistry Research Co., Ltd., Japan.

As the interferon inducers, inducers commonly used such as Poly(I).Poly(C), HVJ, NDV and Con A are all useful in the production of interferon. Other inducers such as Chlamydia, Rickkettsia, mitogens, and lipopolysaccharides may also be used.

Eagle's MEM and RPMI 1640 are generally used as the priming medium and induction medium. In addition, other media such as McCoy 5A, 199, Ham F12, and L15 are applicable.

As the production medium for interferon, not only Eagle's MEM but also buffered salt solutions such as Hanks' solution and Dulbecco's phosphate-buffered saline (PBS$^-$) may be used.

When the cultured cells are exposed to polyhydric alcohol, salt solutions such as Hanks' solution and Earle's solution or the culture medium itself may be used as well as PBS$^-$ as the solvent of the polyhydric alcohol.

The effects of polyhydric alcohol on the production of interferon will now be explained by experimental examples.

EXPERIMENT 1

Effect of polyhydric alcohol on the production of interferon-$\beta$

Human diploid MRC-5 cells (available from Dainippon Pharmaceutical Co., Ltd.) were cultured in Eagle's MEM supplemented with 10% calf serum in a plastic incubation flask at 37° C. under 5% $CO_2$ conditions. After a monolayer of the cells was attained, the medium was changed to Eagle's MEM containing 100 IU/ml of interferon-$\beta$ and 0.1% human serum albumin. Incubation was performed in this medium overnight and further incubation for 5 hours was performed with Poly-(I).Poly(C) and cycloheximide added at final concentrations of 30 μg/ml and 2 μg/ml, respectively. Actinomycin D was added to the culture at a concentration of 1 μg/ml and incubation was performed for another 2 hours. The cells were rinsed twice with PBS$^-$ and incubated overnight in the production medium (Eagle's MEM supplemented with 0.1% human serum albumin). The activity of the produced interferon was measured by the suppression of cytopathic effects (CPE) with FL cell-Sindbis virus system (Kohase et al., Protein, Nucleic acid and Enzyme, Special Issue, No. 25, pp. 355-363, 1981).

The production process described above is a general method to produce interferon-$\beta$ from normal cells using Poly(I).Poly(C) as an inducer. The process is outlined in FIG. 1.

PEG1540 (polyethylene glycol with average molecular weight of 1540) was used as the polyhydric alcohol, and its effect on the production of interferon-$\beta$ was investigated by the methods of FIG. 1. PEG1540 was applied to the culture either by addition into the priming medium and/or production medium at a concentration of 0.3 weight %, or by subjecting the cells to transient exposure to PBS$^-$ containing PEG 1540 before the medium was changed to the priming medium or to the production medium. In addition, the above two methods were combined in some cases. The results are shown in Table 1.

TABLE 1

| Treatment with PEG 1540 | Yield of Interferon-$\beta$ (IU/ml) |
| --- | --- |
| 1. No treatment | 12,700 |
| 2. Addition of PEG 1540 to the priming medium at a concentration of 0.3%* | 25,600 |
| 3. Addition of PEG 1540 to the production medium at a concentration of 0.3%* | 16,200 |
| 4. Rinsing of the cell surface with PBS$^-$ containing 10%* PEG 1540 before changing to the priming medium | 17,500 |
| 5. Rinsing of the cell surface with PBS$^-$ containing 10%* PEG 1540 before changing to the production medium | 22,300 |
| 6. Treatment 2 + Treatment 3 | 27,100 |
| 7. Treatment 2 + Treatment 4 | 27,400 |
| 8. Treatment 2 + Treatment 5 | 28,700 |

*% is expressed by weight

PEG 1540 was added to the priming medium at different concentrations of 0, 0.001, 0.01, 0.1, 1.0 and 10.0 weight %, and the increase in the interferon-$\beta$ production was investigated. The results are shown in Table 2.

TABLE 2

| Concentration of PEG 1540 added to the priming medium (weight %) | Yield of interferon-$\beta$ (IU/ml) |
| --- | --- |
| 0 | 12,700 |
| 0.001 | 13,800 |
| 0.01 | 15,100 |
| 0.1 | 27,900 |
| 1.0 | 24,600 |
| 10.0 | 20,500 |

Various polyhydric alcohols such as hexanetriol, butanediol and pentaerythritol were added to the priming medium, and the increase in the production of interferon-$\beta$ was investigated. The results are shown in Table 3.

TABLE 3

| Polyhydric alcohols added to the priming medium (weight %) | Yield of interferon-$\beta$ (IU/ml) |
| --- | --- |
| none | 11,800 |
| 0.3% PEG 1540 | 27,300 |
| 0.3% Hexanetriol | 19,700 |
| 0.3% Butanediol | 17,100 |
| 0.3% Pentaerythritol | 16,400 |

EXPERIMENT 2

Mouse L929 cells (available from Dainippon Pharmaceutical Co., Ltd.) were inoculated with Eagle's MEM supplemented with 10% calf serum in a plastic flask having a culture area of 150 cm$^2$, and the cells were cultured at 37° C. under 5% $CO_2$ conditions. After the monolayer was attained, interferon was induced by the method illustrated in FIG. 1. PEG 1540 or hexanetriol as the polyhydric alcohol was added to the priming medium at a concentration of 0.3 weight %. For the transient exposure, the cells were rinsed twice with PBS$^-$ containing 10 weight % PEG 1540 before the medium was changed to the production medium. Activity of the produced interferon was measured by suppression of CPE with L929 cell-Sindbis virus system. The results are shown in Table 4.

TABLE 4

| Treatment | Yield of interferon-β (IU/ml) |
|---|---|
| no treatment | 2,090 |
| addition of 0.3%* PEG 1540 to the priming medium | 3,240 |
| addition of 0.3%* Hexanetriol to the priming medium | 2,970 |
| Rinsing of the cell surface twice with PBS⁻ containing 10%* PEG 1540 before changing to the production medium | 2,560 |

*% is expressed by weight

EXPERIMENT 3

Effects of polyhydric alcohol on the production of interferon-α

Lymphoblastoid Namalwa cells (available from Dainippon Pharmaceutical Co., Ltd.) which had been maintained in RPMI 1640 medium supplemented with 5% calf serum were primed overnight in RPMI 1640 medium containing 100 IU/ml of interferon-α and 0.1% human serum albumin. HVJ was added to the culture at a concentration of 100 HAV/ml and the culture was incubated overnight. Then HVJ was inactivated under an acidic condition of pH 2. After the medium was neutralized to pH 7, the yield of interferon was measured.

Figure 2:
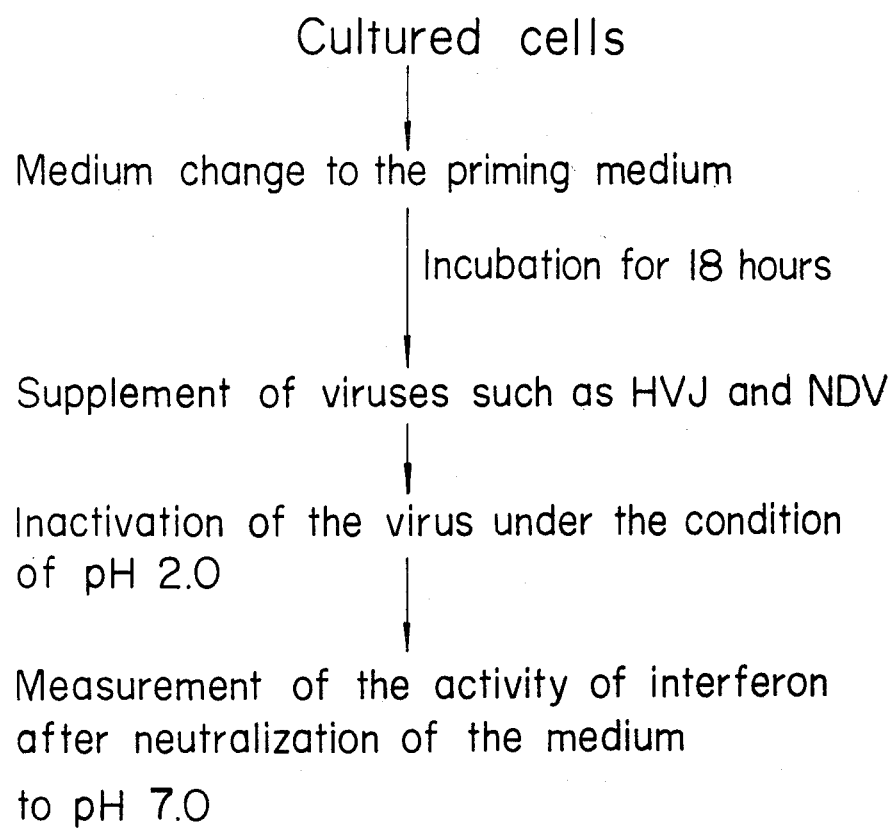
FIG. 2 is a flow chart showing a general process of producing interferon-α which is employed in Experiment 3.

The process of production described above is a general method to produce interferon-α from leukocytes or lymphoblastoid cells. The process is outlined in FIG. 2.

PEG 1540 as the polyhydric alcohol was added at a concentration of 0.3 weight % to the priming medium, or for transient exposure the cells were rinsed twice with PBS⁻ containing 10 weight % PEG 1540 before the medium was changed to the priming medium. The results are shown in Table 5.

TABLE 5

| Treatment | Yield of interferon-α (IU/ml) |
|---|---|
| no treatment | 1,740 |
| addition of 0.3%* PEG 1540 to the priming medium | 3,620 |
| Rinsing of the cell surface with PBS⁻ containing 10%* PEG 1540 before changing to the priming medium | 2,980 |

*% is expressed by weight

In the transient exposure described above, the concentration of PEG 1540 was varied among 0.1, 1.0, 10, 30, and 60 weight % in order to investigate the effect on the increase in the interferon-α production. The results are shown in Table 6.

TABLE 6

| Concentration of PEG 1540 for the transient exposure before changing to the priming medium (weight %) | Yield of interferon-α (IU/ml) |
|---|---|
| none | 1,740 |
| 0.1% | 1,960 |
| 1.0% | 2,170 |
| 10% | 2,980 |
| 30% | 2,950 |
| 60% | 2,630 |

EXPERIMENT 4

Effects of polyhydric alcohols on the production of interferon-γ

Leukocytes were isolated from the peripheral blood of healthy adult volunteers by Ficoll-Hypaque gradient. The leukocytes were cultured in plastic dishes and the cells which did not attach to the dish surface were collected. These cells were suspended in RPMI 1640 medium supplemented with 0.1% human serum albumin. Con A was added to the suspension at a concentration of 5 μg/ml and incubation was performed for 48 hours.

Figure 3:
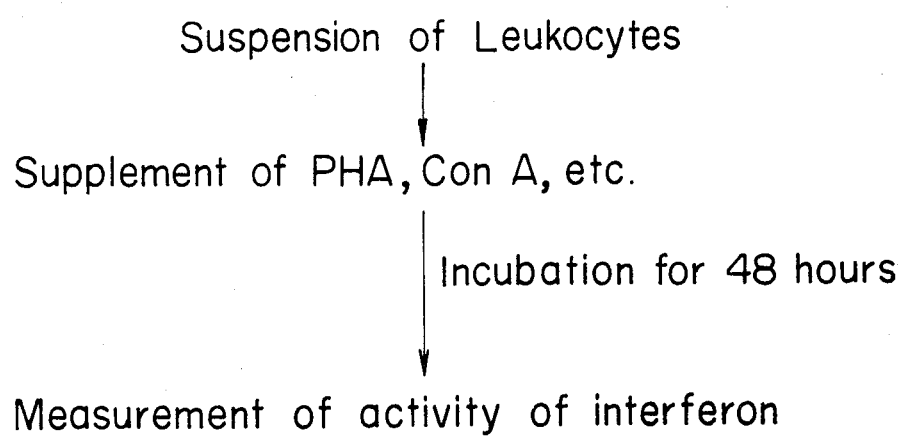
FIG. 3 is a flow chart showing a general process of producing interferon-γ which is employed in Experiment 4.

The process of production described above is a general method to produce interferon-γ. The process is outlined in FIG. 3.

PEG 1540 was used as the polyhydric alcohol and added at a concentration of 0.3 weight % to the RAM 1640 medium supplemented with 0.1% human serum albumin. The results are shown in Table 7.

TABLE 7

| PEG added to leukocyte suspension (weight %) | Yield of interferon-γ (U/ml) |
|---|---|
| none | 790 |
| 0.3% PEG 1540 | 1,420 |

The present invention is further explained by the following examples which are not to be construed to limit the scope of the invention. cl EXAMPLE 1

Production of interferon-α

Namalwa cells were inoculated in RPMI 1640 medium supplemented with 5% calf serum at $3 \times 10^5$ cells/ml and cultured for 3 days. After that period, the cells were rinsed with PBS⁻ containing 10 weight % PEG 1540. Then the cells were suspended at a concentration of $1 \times 10^6$ cells/ml in RPMI 1640 medium containing 100 IU/ml of interferon-α, 0.1% human serum albumin and 0.3 weight % PEG 1540. After 18 hours of incubation, 100 HAV/ml of HVJ was added and incubation was further performed overnight. Then HVJ was inactivated under an acidic condition of pH 2 by the addition of HCl. The activity of the interferon-α was measured after the neutralization of the medium to pH 7. The yield of interferon-α was 4,700 IU/ml.

EXAMPLE 2

Production of interferon-β

WI-38 cells (available from Dainippon Pharmaceutical Co., Ltd.) were inoculated at $5 \times 10^6$ cells/150 cm² flask in Eagle's MEM medium supplemented with 10% calf serum and cultured for 5 days. Overnight priming was performed in MEM medium containing 100 IU/ml of interferon-β, 0.1% human serum albumin, and 0.5 weight % PEG 1540. Interferon was induced by the superinduction method using Poly(I).Poly(C), cycloheximide, and actinomycin D. The cell surface was rinsed with 10 weight % butanediol solution before the medium was changed to the production medium which consists of Earle's solution containing 0.1% human serum albumin. The yield of interferon-β was 37,500 IU/ml.

What is claimed is:

1. In a method for producing interferon by culturing interferon-producing cells in a medium in the presence of an interferon inducer under conditions suitable for the formation of interferon and recovering the interferon, the improvement comprising treating said interferon-producing cells at a priming stage in a priming medium with an interferon stimulating amount of a water soluble polyhydric alcohol which has two or more alcoholic hydroxyl groups, said at least one polyhydric alcohol being selected from the group consisting of polyethylene glycol, diol-type polypropylene glycol, triol-type polypropylene glycol, ethylene glycol, propanediol, butanediol, butanetriol, butanetetrol, pentanediol, pentaerythritol and hexanetriol.

2. A method for producing interferon according to claim 1, wherein said cells are selected from the group consisting of human diploid MRC-5 cells, hyman lymphoblastoid Namalva cells, human T cells, mouse L929 cells, WI-38 cells, IMR-90 cells, MG-63 cells, Flow 1000 cells, Flow 4000 cells, Ball-1 cells, RK-13 cells, MDBK cells and mammalian primary culture cells.

3. A method for producing interferon according to claim 1, wherein said inducer is selected from the group consisting of Poly(I).Poly(C), HVJ, NDV, Concanavalin A, Chlamydia, Rickkettsia, mitogens and lipopolysaccharides.

4. A method for producing interferon according to claim 1, wherein said mixture of two or more said alcohols is used.

5. A method for producing interferon according to claim 1, wherein said polyhydric alcohol is polyethylene glycol.

6. A method for producing interferon according to claim 1, wherein said interferon stimulating amount of the polyhydric alcohol is 0.001 to 30% by weight.

7. A method for producing interferon according to claim 6, wherein said interferon stimulating amount of said polyhydric alcohol is 0.1 to 5% by weight.

8. In a method for producing interferon by culturing interferon-producing cells in a medium in the presence of an interferon inducer under conditions suitable for the formation of interferon and recovering the interferon, the improvement comprising rinsing said interferon producing cells with a rinsing solution of an interferon stimulating amount of a water soluble polyhydric alcohol which has two or more alcoholic hydroxyl groups when the medium is changed to a priming medium, an induction medium, or a production medium for culturing said interferon-producing cells.

9. A method for producing interferon according to claim 8, wherein said interferon stimulating amount of polyhydric alcohol is 0.1 to 60% by weight.

10. A method for producing interferon according to claim 9, wherein said interferon stimulating amount of said polyhydric alcohol is 1 to 30% by weight.

11. A method for producing interferon according to claim 8, wherein said polyhydric alcohol is selected from the group consisting of polyethylene glycol, diol-type polypropylene glycol, triol-type polypropylene glycol, ethylene glycol, propanediol, butanediol, butanetriol, butanetetrol, pentanediol, pentaerythritol and hexanetriol.

12. A method for producing interferon according to claim 11, wherein said polyhydric alcohol is used at a concentration of 0.1 to 60% by weight.

13. A method for producing interferon according to claim 12, wherein the concentration of said polyhydric alcohol is 1 to 30% by weight.

14. A method for producing interferon according to claim 11, wherein said mixture of two or more said alcohols is used.

15. A method for producing interferon according to claim 14, wherein said polyhydric alcohol is used at a concentration of 0.1 to 60% by weight.

16. A method for producing interferon according to claim 15, wherein the concentration of said polyhydric alcohol is 1 to 30% by weight.

17. In a method for producing interferon by culturing interferon-producing cells in a medium in the presence of an interferon inducer under conditions suitable for the formation of interferon and recovering the interferon, the improvement comprising treating at a priming stage in a priming medium said interferon-producing cells with an interferon stimulating amount of a water soluble polyhydric alcohol which has two or more alcoholic hydroxyl groups, and rinsing said interferon-producing cells with a rinsing solution of a water soluble polyhydric alcohol which has two or more alcoholic hydroxyl groups when the medium is changed to a priming medium, an induction medium or a production medium for culturing said interferon-producing cells.

18. A method for producing interferon according to claim 17, wherein the interferon stimulating amount of said polyhydric alcohol in said priming medium is 0.001 to 30% by weight and the interferon stimulating amount of said polyhydric alcohol in said rinsing solution is 0.1 to 60% by weight.

19. A method for producing interferon according to claim 18, wherein the interferon stimulating amount of said polyhydric alcohol in the priming medium is 0.1 to 5% by weight and the interferon stimulating amount of the polyhydric alcohol in the rinsing solution is 1 to 30% by weight.

20. A method for producing interferon according to claim 17, wherein said polyhydric alcohol is selected from the group consisting of polyethylene glycol, diol-type polypropylene glycol, triol-type polypropylene glycol, ethylene glycol, propanediol, butanediol, butanetriol, butanetetrol, pentanediol, pentaerythritol and hexanetriol.

21. A method for producing interferon according to claim 20, wherein the interferon stimulating amount of said polyhydric alcohol in said priming medium is 0.001 to 30% by weight and the interferon stimulating amount of said polyhydric alcohol in said rinsing solution is 0.1 to 60% by weight.

22. A method for producing interferon according to claim 21, wherein the interferon stimulating amount of said polyhydric alcohol in the priming medium is 0.1 to 5% by weight and the interferon stimulating amount of the polyhydric alcohol in the rinsing solution is 1 to 30% by weight.

23. A method for producing interferon according to claim 20, wherein said mixture of two or more said alcohols is used.

24. A method for producing interferon according to claim 23, wherein the interferon stimulating amount of said polyhydric alcohol in said priming medium is 0.001 to 30% by weight and the interferon stimulating amount of said polyhydric alcohol in said rinsing solution is 0.1 to 60% by weight.

25. A method for producing interferon according to claim 24, wherein the interferon stimulating amount of said polyhydric alcohol in the priming medium is 0.1 to 5% by weight and the interferon stimulating amount of the polyhydric alcohol in the rinsing solution is 1 to 30% by weight.

* * * * *